United States Patent [19]

Senior et al.

[11] 4,324,907

[45] Apr. 13, 1982

[54] EXTRACTION PROCESS

[75] Inventors: Peter J. Senior, Middlesbrough; Leonard F. Wright, Stockton-on-Tees; Barry Alderson, Billingham, all of England

[73] Assignee: Imperial Chemical Industries Limited, London, England

[21] Appl. No.: 125,483

[22] Filed: Feb. 22, 1980

[30] Foreign Application Priority Data

May 8, 1979 [GB] United Kingdom ............... 15858/79

[51] Int. Cl.$^3$ ..................... C07C 67/56; C07C 69/675
[52] U.S. Cl. ..................................... 560/185; 210/639
[58] Field of Search ......................... 560/185; 435/146

[56] References Cited

U.S. PATENT DOCUMENTS 3,036,959 5/1962 Baptist ................................. 560/185
3,044,942 7/1962 Baptist ................................. 560/185
3,107,172 10/1973 Baptist et al. .
3,275,610 9/1966 Coty ..................................... 526/199

OTHER PUBLICATIONS

Chemical Abstracts, vol. 74 (1971), #54,281p.
Chemical Abstracts, vol. 85 (1976), #178,134q.

*Primary Examiner*—Natalie Trousof
*Assistant Examiner*—L. Hendriksen
*Attorney, Agent, or Firm*—Cushman, Darby & Cushman

[57] ABSTRACT

Poly($\beta$-hydroxybutyric acid) is separated from bacterial cells by drying a finely divided stream or spray of an aqueous suspension of the cells with a gas heated to above 100° C. and then extracting the PHB, preferably after a lipid extraction step with a solvent such as a partially halogenated hydrocarbon such as 1,2-dichloroethane, chloroform or dichlorom

10 Claims, No Drawings

EXTRACTION PROCESS

This invention relates to an extraction process and in particular to a process of extracting poly($\beta$-hydroxy butyric acid), hereinafter referred to as PHB from microbial cells.

It has been known since the 1920's that many microorganisms are capable of accumulating granules of PHB within their cells as an energy reserve material. It has been proposed in U.S. Pat. No. 3,107,172 to dry such PHB containing bacterial cells, for example by spray drying, and to use the resultant dried cells as moulding compositions. Suggestions have also been made to extract PHB from bacterial cells and to use it as a plactics material, but methods so far disclosed have not been economically acceptable.

In order to extract the PHB, it is generally necessary to contact the bacterial cells with a solvent in which PHB is soluble to leach out the PHB from the remainder of the bacterial cell material. Some bacteria, for example members of the genus Azotobacter readily yield up their PHB to the extraction solvent, whereas other bacterial, eg Pseudomonadaceae have more robust cells and require a cell disruption step prior to contact with the extraction solvent.

Methods of extraction previously proposed have included the steps of harvesting the bacterial cells from the aqueous fermentation medium, eg by centrifugation, to give a mass of wet cells which are then contacted with acetone to effect drying and cell breakage. After removal of the acetone, the PHB is extracted with a suitable solvent, eg pyridine (U.S. Pat. No. 3,036,959) or a dichloromethane/ethanol mixture (U.S. Pat. No. 3,044,942). Such methods have the advantage that in addition to effecting drying and cell breakage, acetone also extracts lipids and pigments (if any) which would otherwise contaminate the product. However treatment of a mass of wet cells with acetone to effect drying and cell breakage is not economic on a large scale.

Another method is described in U.S. Pat. No. 3,275,610 wherein a dispersion of bacterial cells in water is subjected to ultrasonic vibration to rupture the cells followed by centrifugation and drying before extraction with a solvent such as chloroform. After separation of the PHB from the chloroform solution, the PHB is washed to extract lipids therefrom.

It has also been proposed in U.S. Pat. No. 4,101,533 to extract PHB from dried cells, or directly from a wet mass of cells harvested from the fermentation medium by centrifugation, by heating the cells with certain cyclic carbonate solvents.

It is also possible to extract PHB directly from the aqueous cell suspension produced by fermentation, preferably after some concentration, by contact with certain solvents such as chloroform, dichloromethane, or 1,2-dichloroethane with, where necessary, a cell disruption step, eg milling, prior to contact with the solvent. However the solvent, and extraction conditions, have to be selected with care to avoid undue uptake by the solvent of non-PHB material particularly lipids and pigment (if any) present in the bacterial cell. Not only does such non-PHB material contaminate the product and so present purification difficulties but also the co-extraction of lipids may tend to result in the formation of a relatively stable emulsion between the solvent and aqueous phases rendering separation thereof difficult. With such a direct extraction process, a separate lipid extraction step prior to contact with the PHB extraction solvent is generally not practical as the solvents that extract lipids would need to be removed, together with the lipids, prior to contact with the PHB extraction solvent and, because the more effective lipid solvents tend to be water miscible, such removal of the lipid solution presents practical difficulties.

We have now found that PHB can be extracted from bacterial cells by a particularly simple process amenable to large scale operation.

According to the present invention we provide a process for the extraction of PHB from an aqueous suspension of PHB-containing bacterial cells comprising introducing said suspension in finely divided form into a current of gas heated to a temperature of at least 100° C. to evaporate the water from said suspension, collecting the resultant dried bacterial cells, extracting the PHB therefrom by contact with an extraction solvent which is a liquid that is a solvent for the PHB in the bacterial cells, and separating the extraction solvent having the PHB dissolved therein from the bacterial cell residue.

We have found that such a drying process sufficiently weakens the bacterial cells to enable the PHB to be extracted without the necessity for any separate cell breakage step. While for particularly robust bacteria a separate cell breakage step, eg milling, prior to drying may be desirable to increase the yield of PHB extracted, we have found that generally such as separate cell breakage step prior to drying is not necessary and indeed is best avoided if possible as drying milled dispersions gives rise to difficulties such as build-up in the drier.

In the process of the invention it is preferred to subject the cells to a lipid extraction step prior to extraction with the PHB extraction solvent. Thus the dried cells may be extracted with a lipid/pigment solvent such as acetone, methanol, ethanol, butanol, hexane, or petroleum ether, followed by separation of the solvent containing dissolved lipids/pigment from the cells prior to contacting the cells with the PHB extraction solvent. The lipid/pigment extraction is preferably performed by refluxing the dried cells with the solvent. Acetone and methanol are the preferred lipid extraction solvents. The lipid/pigment extraction solvent may be used in admixture with another PHB non-solvent such as diethyl ether.

It will be appreciated that this lipid extraction may also give rise to some further weakening or breakage of the cells thus facilitating the subsequent extraction of the PHB.

In the process of the invention the cells are separated from the aqueous suspension by a drying process involving introducing the cell suspension in finely divided form, eg as a spray or fine stream, into a current of gas, eg air, heated to a temperature of at least 100° C. Preferably the suspension is introduced via a spray or atomising nozzle. Such drying processes are well known and include spray and flash drying.

The heated gas current evaporates off the water which is carried away by the gas stream leaving the dried cells which are collected for extraction with the PHB extraction solvent.

The gas inlet temperature may be in the range 100° C. to 500° C. and is preferably in the range 120° C. to 250° C.

Suitable PHB extraction solvents include pyridine, cyclic carbonates and, particularly, partially halogenated hydrocarbons such as chloroform, dichloromethane and 1,2-dichloroethane. 1,2-Dichloroethane is not normally considered to be a solvent for PHB because PHB, after separation from bacterial cells, does not readily, or completely, dissolve in 1,2-dichloroethane. Thus, whereas the PHB solution separated from the bacterial cell residue appears to be a single phase, a solution made by re-dissolving PHB in 1,2-dichloroethane after precipitation is, except when very dilute, pearly in appearance, and PHB that has been precipitated and dried does not readily re-dissolve in that solvent. It is therefore surprising that such a solvent should be effective for extracting PHB from cells. For efficient extraction, the extraction is preferably conducted at a temperature above 40° C. Thus temperatures up to, and including, the solvent boiling point may be used and superatmospheric pressures may be employed to enable temperatures in excess of the solvent boiling point at atmospheric pressure to be employed.

Where, as is not preferred for reasons described hereinbefore, the cell suspension is subjected to a cell disruption step, eg milling, prior to drying, the extraction temperature should be below 40° C. to avoid undue uptake of lipids. Thus if a milled dispersion is dried and extractd with a hot solvent, on precipitation of the PHB from the solvent, a gelatinous sticky mass tends to be formed. Where however a lipid extraction step is employed prior to contact with the PHB solvent, the extraction with the PHB solvent may be conducted at temperatures above 40° C.

The weight of PHB extraction solvent used is preferably 10 to 100 times the cell dry weight. The use of smaller amounts of solvent may reduce the extraction efficiency of crude PHB and may give solutions of excessive viscosity while the use of larger amounts is uneconomic. The amount of solvent is preferably such that the extracted solution contains 0.5 to 5%, particularly 1 to 2% by PHB by weight.

The contacting time for extraction should be a compromise to give adequate extraction without being uneconomically lengthy.

Separation of the cell residue from the PHB-containing solution may be effected by a simple filtration or centrifugation step. If the cells are subjected to a lipid extraction prior to extraction of the PHB, the filtration of the PHB solution from the cell residue tends to be particularly facile and can be effected using relatively coarse filters.

After separation of the PHB-containing extraction solvent from the bacterial cell residue, the PHB solution may be further filtered, if desired, to remove any suspended bacterial fragments. Such filtration is preferably conducted using a filter, eg a glass fibre filter, having a pore size of less than 5 $\mu$m, preferably less than 2 $\mu$m.

The separated PHB-containing solution can be used directly, preferably after filtration, for making solvent cast articles such as coatings, films or fibres or the solution may be treated further to separate solid PHB, for example by evaporation of the solvent or by precipitation by addition of the PHB-containing solution to a liquid in which PHB is insoluble and with which the solvent is miscible. Examples of suitable liquids include petroleum ether and methanol/water mixtures. The PHB may be purified, if desired, by washing with methanol or acetone.

After extraction of the PHB, the bacterial cell residues may be further refined for other uses, eg as a feedstuff or fertilizer.

Any bacteria that are capable of accumulating PHB may be used to produce the PHB-containing bacterial cells. A paper by Senior et al in Advances in Microbial Physiology 1973 10 203–266 lists the bacteria published up to June 1972 and others are described in U.S. Pat. No. 3,072,538 (Rhizobium mutants) and UK Pat. No. 1,535,632 (especially mutants of *Alcaligenes eutrophus, Bacillus megaterium, Zoogloea ramigera,* and *Mycoplana rubra*). Among the preferred bacteria are Azotobacter, especially chroococcum, Alcaligenes, especially eutrophus, and the Pseudomonadaceae, especially Pseudomonas AM 1 and *Methylobacterium organophilum.*

Among such bacteria are those capable of metabolising one or more of a variety of substrates, for example carbohydrates, ethanol, methanol, polyhydric alcohols, carbon dioxide/hydrogen, and carboxylic acids, and, according to the substrate used, may grow aerobically or anaerobically. The invention is of particular utility in separating PHB from bacterial cells of the *Pseudomonadaceae* grown under aerobic fermentation conditions on an alcohol, particularly methanol, substrate. The invention is also of particular utility in separating PHB from Azotobacter grown on a water soluble carbohydrate such as sucrose or glucose.

The cell suspension produced by the fermentation process will typically contain 20 to 55 g $l^{-1}$ biomass solids. Where the suspension is extracted with a pigment/lipid extraction solvent without an intermediate drying step, for efficient extraction, the cell suspension preferably has a concentration of 5 to 15% by weight biomass solids. The cell suspension is preferably concentrated, eg by centrifugation, to within this range where this is necessary. (The cell suspension as produced in the fermentation process may already have a concentration within this range: however even in such cases some concentration may be desirable). Spray or flash drying the cell suspension sufficiently weakens the cells to allow the PHB to be extracted without any other cell disruption step. Hence no separate cell disruption step is required where the aqueous cell suspension is spray or flash dried prior to contact with the extraction solvent.

The invention is illustrated by the following examples in which all percentages are by weight.

EXAMPLE 1 (Comparative)

This example demonstrates that simple air drying does not weaken the cells sufficiently to allow efficient PHB extraction.

1000 ml of an aqueous suspension of *Methylobacterium organophilum* (NCIB 11483—which is further described in our UK Patent application No. 79 06078) containing 60 g biomass solids of which 36% was PHB was centrifuged to give a pellet of wet bacterial cells.

(NCIB No. refers to the number of the culture deposited at the National Collection of Industrial Bacteria, Torry Research Station, Aberdeen, Scotland).

The pellet was then dried in a fluid bed drier at 40° C. for 10 hours.

10 g of the resultant dried cells were suspended in 500 ml of 1,2-dichloroethane at room temperature for 15 minutes and then the solvent phase was removed by centrifugation and decanting. This solution was added to 3000 ml of a methanol/water mixture (4 volumes of methanol to 1 volume of water) with vigorous stirring to precipitate crude PHB. The precipitate was collected on a filter and dried in vacuo at 50° C. The yield of crude PHB was less than 0.5%.

The above experiment was repeated but the dry cells were sheared with 1,2-dichloroethane in a Silverson mixer at room temperature for 15 minutes. The yield of crude PHB was 1.4%.

The above experiment was repeated but the dry cells were refluxed with the 1,2-dichloroethane at 83° C. for 15 minutes. The yield of crude PHB (purity 94.5%) was 29%.

(Yields are calculated herein as $$\frac{\text{weight of crude PHB recovered}}{\text{dry weight of cells used}} \times \frac{100}{\text{\% PHB in cells}} \times 100)$$

EXAMPLE 2

5000 ml of the aqueous suspension of bacterial cells used in Example 1 was spray dried at a suspension feed rate of 5000 ml $hr^{-1}$, an air inlet temperature of 150° C., an air outlet temperature of 80° C. and an air flow rate of 300 $m^3$ $hr^{-1}$.

20 g of the spray dried cells were suspended in 1000 ml of 1,2-dichloroethane at room temperature for 15 minutes. The cell debris was removed by filtration through a Whatman 541 paper filter. The PHB was recovered from the solution by adding the latter to 5000 ml of a methanol/water mixture (4 vol. methanol:1 vol. water) with vigorous stirring. The precipitate was collected on a filter. The yield of crude PHB was 5.7%.

The above experiment was repeated except that the dried cells were sheared with the 1,2-dichloroethane in a Silverson mixer at room temperature for 15 minutes. The yield of crude PHB (purity 98.2%) was 12.2%.

The above experiment was repeated except that the dried cells were refluxed with the 1,2-dichloroethane at 83° C. for 15 minutes. The yield of crude PHB (purity 93.6%) was 98.3%. The precipitate was washed 5 times with 500 ml aliquots of methanol and then dried at 106° C. The purity of the washed PHB was 98.7%.

EXAMPLE 3

20 g of the spray dried cells as used in Example 2 were refluxed for 5 minutes with 600 ml of acetone at 56° C. to extract lipids and pigment and then the acetone removed by filtration. The residual cells were then sheared for 15 minutes at room temperature with 1000 ml of 1,2-dichloroethane in a Silverson mixer. The resultant solution was filtered from the cell residue using a Whatman 541 paper filter and the PHB was then precipitated by adding the solution to 5000 ml of a methanol/water mixture (4 vol. methanol; 1 vol. water) with vigorous stirring. The precipitate was collected on a filter.

The yield of crude PHB (purity 96.7%) was 43.2%.

The above procedure was repeated save that instead of shearing the acetone extracted cells with 1,2-dichloroethane, the acetone extracted cells were refluxed for 15 minutes with 1,2-dichloroethane at 83° C.

The yield of crude PHB (purity 98.4%) was 95%.

It is thus seen that while the acetone extraction further weakened the spray dried cells to allow more PHB to be extracted by cold 1,2-dichloroethane, spray drying alone sufficiently weakened the cells to permit efficient extraction of the PHB by boiling 1,2-dichloroethane. The acetone extraction did, however, improve the purity of the extracted PHB.

EXAMPLE 4

An aqueous suspension of cells of *Azotobacter chroococcum* (NCIB 9125) containing 60 g $l^{-1}$ biomass solids of which 37.8% was PHB was spray dried, acetone extracted, extracted with 1,2-dichloroethane under reflux, and precipitated using the conditions described in Example 3 above.

The yield of crude PHB (purity 98%) was 89.4%.

EXAMPLE 5

Example 4 was repeated using methanol instead of acetone as the lipid extraction solvent and dichloromethane instead of 1,2-dichloroethane as the PHB extraction solvent. The yield of PHB (purity 98%) was in excess of 95%.

Similar results were obtained using chloroform as the PHB extraction solvent.

We claim:

1. A process for the extraction of poly($\beta$-hydroxy butyric acid) (PHB) from an aqueous suspension of PHB-containing bacterial cells comprising:
   introducing an aqueous suspension of PHB-containing bacterial cells in finely divided form into a current of gas heated to a temperature of at least 100° C. to evaporate the water from the suspension,
   collecting the resultant dried bacterial cells,
   extracting the PHB therefrom by contact with an extraction solvent which is a liquid that is a solvent for the PHB in the bacterial cells, and
   separating the extraction solvent from the PHB dissolved therein from the bacterial cell residue.

2. A process according to claim 1 wherein, prior to contact of the dried cells with the extraction solvent, the dried cells are contacted with a liquid in which PHB is not soluble but in which lipids and/or pigment in the bacterial cells is soluble.

3. A process according to claim 2 in which the liquid in which PHB is not soluble is acetone or methanol.

4. A process according to claim 1 in which the gas is heated to a temperature in the range 100° to 500° C.

5. A process according to claim 4 in which the gas is heated to a temperature in the range 120° to 250° C.

6. A process according to claim 1 in which the extraction solvent is a partially halogenated hydrocarbon.

7. A process according to claim 6 in which the extraction solvent is 1,2-dichloroethane, dichloromethane, or chloroform.

8. A process according to claim 1 in which the dried cells are contacted with the extraction solvent at a temperature above 40° C.

9. A process according to claim 1 in which the weight of extraction solvent is 10 to 100 times the cell dry weight.

10. A process according to claim 1 in which the extraction solvent containing the dissolved PHB is separated from the bacterial cell residue and then added to a liquid in which PHB is insoluble and with which the extraction solvent is miscible to precipitate the PHB.

* * * * *